United States Patent
Baker et al.

(10) Patent No.: US 8,017,108 B2
(45) Date of Patent: Sep. 13, 2011

(54) CONDITIONING COMPOSITION COMPRISING AMINOSILICONE

(75) Inventors: Ellen Schmidt Baker, Cincinnati, OH (US); Nobuaki Uehara, Kobe (JP); Robert Lee Wells, Cincinnati, OH (US); Kendrick Jon Hughes, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1138 days.

(21) Appl. No.: 10/946,957

(22) Filed: Sep. 22, 2004

(65) Prior Publication Data

US 2005/0063934 A1 Mar. 24, 2005

Related U.S. Application Data

(60) Provisional application No. 60/505,726, filed on Sep. 24, 2003, provisional application No. 60/543,219, filed on Feb. 10, 2004.

(51) Int. Cl.
*A61Q 5/12* (2006.01)

(52) U.S. Cl. .................... 424/70.12; 424/70.28

(58) Field of Classification Search .................. None
See application file for complete search history.

(56) References Cited

U.S. PATENT DOCUMENTS

| | | | |
|---|---|---|---|
| 4,450,152 A | 5/1984 | Ona et al. | |
| 5,989,533 A * | 11/1999 | Deegan et al. | 424/70.28 |
| 6,610,280 B2 | 8/2003 | Ainger et al. | |
| 2002/0012645 A1 * | 1/2002 | Midha et al. | 424/70.2 |
| 2002/0015686 A1 | 2/2002 | Pyles | |
| 2002/0146381 A1 | 10/2002 | Aeby | |
| 2003/0003073 A1 | 1/2003 | Muller | |
| 2003/0039623 A1 | 2/2003 | Pyles | |
| 2003/0219399 A1 | 11/2003 | Hammond et al. | |
| 2003/0224954 A1 * | 12/2003 | Wells et al. | 510/119 |

FOREIGN PATENT DOCUMENTS

| | | |
|---|---|---|
| EP | 0460683 A2 | 12/1992 |
| JP | 1999029791 | 2/1999 |
| JP | 2001-163733 | 6/2001 |
| JP | 2002-226326 | 8/2002 |
| JP | 2003-95891 | 4/2003 |
| JP | 3499063 B | 2/2004 |
| WO | WO 99/03447 A1 | 1/1999 |
| WO | WO 99/49836 A1 | 10/1999 |
| WO | WO 00/48556 A1 | 8/2000 |
| WO | 02/092034 * | 11/2002 |
| WO | WO 03/066007 A1 | 8/2003 |
| WO | WO 03/075866 A1 | 9/2003 |
| WO | WO 03/092034 A1 | 11/2003 |
| WO | WO 03/092637 A1 | 11/2003 |
| WO | WO 03/092638 A1 | 11/2003 |
| WO | WO 03/092639 A1 | 11/2003 |

* cited by examiner

*Primary Examiner* — Jyothsna Venkat
(74) *Attorney, Agent, or Firm* — Angela K. Haughey; Laura L. Whitmer

(57) ABSTRACT

A conditioning composition containing an aminosilicone having a viscosity of from about 1,000 cs to about 1,000,000 cs, and less than about 0.5% nitrogen by weight of the aminosilicone, a cationic surfactant, a high melting point fatty compound, and an aqueous carrier. These compositions may optionally comprise a low viscosity fluid. The present invention is further directed to a method of making the conditioning composition and a method of using the conditioning composition.

4 Claims, No Drawings

CONDITIONING COMPOSITION COMPRISING AMINOSILICONE

CROSS REFERENCE TO RELATED APPLICATION(S)

This application claims the benefit of U.S. Provisional Application Nos. 60/505,726, filed Sep. 24, 2003, and 60/543,219, filed Feb. 10, 2004.

FIELD

The present invention relates to conditioning compositions containing an aminosilicone, a cationic surfactant, a high melting point fatty compound, and an aqueous carrier. These compositions provide improved hair conditioning performance such as increasing hair shine, smoothness, and softness.

BACKGROUND

Human hair becomes soiled due to its contact with the surrounding environment and from the sebum secreted by the scalp. The soiling of hair causes it to have a dirty feel and an unattractive appearance. The soiling of the hair necessitates shampooing with frequent regularity.

Shampooing cleans the hair by removing excess soil and sebum. However, shampooing can leave the hair in a wet, tangled, and generally unmanageable state. Once the hair dries, it is often left in a dry, rough, lusterless, or frizzy condition due to removal of the hair's natural oils and other natural conditioning and moisturizing components. The hair can further be left with increased levels of static upon drying, which can interfere with the combing and result in a condition commonly referred to as "fly-away hair", or contribute to an undesirable phenomenon of "split ends". Further, chemical treatments, such as perming, bleaching, or coloring hair, can also damage hair and leave it dry, rough, lusterless, and damaged.

A variety of approaches have been developed to condition the hair. A common method of providing conditioning benefits to the hair is through the use of conditioning agents such as cationic surfactants and polymers, high melting point fatty compounds, low melting point oils, silicone compounds, and mixtures thereof.

However, there still exists the opportunity to increase the conditioning benefits delivered through the conditioning compositions. There still exists a need for hair-conditioning compositions which provide improved silicone deposition and/or improved conditioning via friction reduction. Particularly, a need still exists to provide a conditioning composition with enhanced benefits such as hair shine, softness, dry hair smoothness, hair strand alignment (e.g. minimize frizziness), and ease of combing. Also, a need still exists for a conditioning composition that is effective for providing conditioning benefits to hair that is damaged by natural, environmental factors, as well as chemical hair treatments.

SUMMARY

The present invention can provide inherently more effective conditioning products, thus providing improved conditioning benefits such as hair shine, softness, dry hair smoothness, hair strand alignment (e.g., minimize frizziness), and ease of combing. Further, the present invention can provide enhanced silicone deposition and/or improved conditioning via friction reduction. Also, the present invention is effective for providing conditioning benefits to hair that is damaged by natural, environmental factors such as shampooing, as well as chemical hair treatments such as bleaching, coloring, or perming.

The present invention is directed to a conditioning composition containing from about 0.1% to about 20% of an aminosilicone having a viscosity of from about 1,000 cs to about 1,000,000 cs, and less than about 0.5% nitrogen by weight of the aminosilicone; from about 0.1% to about 10% of a cationic surfactant; from about 0.1% to about 20% of a high melting point fatty compound; and an aqueous carrier. The present invention may optionally include a low viscosity fluid. The present invention is further directed to a method of using the conditioning composition.

Another embodiment of the invention relates to a method of making a conditioning composition comprising mixing together a previously formed blend of aminosilicone and a low viscosity fluid, wherein the aminosilicone has less than about 0.5% nitrogen by weight of the aminosilicone; a cationic surfactant; a high melting point fatty compound; and an aqueous carrier.

DETAILED DESCRIPTION

The essential components of the conditioning composition are described below. Also included is a nonexclusive description of various optional and preferred components useful in embodiments of the present invention. While the specification concludes with claims that particularly point out and distinctly claim the invention, it is believed that the present invention will be better understood from the following description.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified. The term "weight percent" may be denoted as "wt. % herein.

All molecular weights as used herein are weight average molecular weights expressed as grams/mole, unless otherwise specified.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "cs" means centistokes.

The term "conditioning composition" as used herein, unless otherwise specified, refers to the compositions of the present invention, wherein the compositions are intended to include those compositions for topical application to the hair or scalp.

The term "aminosilicone" as used herein, unless otherwise specified, refers to a silicone containing at least one primary amine, secondary amine, tertiary amine, or a quaternary ammonium group.

The term "high melting point fatty compound" as used herein, unless otherwise specified, is a compound having the general formula R—X, wherein R is an aliphatic (e.g. fatty chain) and X is a functional group (e.g. alcohol, acid, or derivative), wherein the compounds have a melting point of 25° C. or higher.

The compositions of the present invention preferably have a pH of from about 3 to about 8, preferably from about 4 to about 7 when measured on the neat product.

A. Aminosilicone

The conditioning composition of the present invention includes an aminosilicone. An aminosilicone is a silicone containing at least one primary amine, secondary amine, tertiary amine, or a quaternary ammonium group. Preferred aminosilicones may have less than about 0.5% nitrogen by weight of the aminosilicone, more preferably less than about 0.2%, more preferably still, less than about 0.1%. Higher levels of nitrogen (amine functional groups) in the amino silicone tend to result in less friction reduction, and consequently less conditioning benefit from the aminosilicone.

Preferably the silicones used in the present invention have a particle size of less than about 50μ once incorporated into the final composition. The particle size measurement is taken from dispersed droplets in the final composition. Particle size may be measured by means of a laser light scattering technique, using a Horiba model LA-910 Laser Scattering Particle Size Distribution Analyzer (Horiba Instruments, Inc).

In a preferred embodiment, the aminosilicone has a viscosity of from about 1,000 cs to about 1,000,000 cs, more preferably from about 10,000 cs to about 700,000 cs, more preferably from about 50,000 cs to about 500,000 cs, still more preferably from about 100,000 cs to about 400,000 cs. The viscosity of aminosilicones discussed herein is measured at 25° C.

The aminosilicone is contained in the composition of the present invention at a level by weight of from about 0.1% to about 20%, preferably from about 0.5% to about 10%, more preferably from about 1% to about 6%.

Examples of preferred aminosilicones for use in embodiments of the subject invention include, but are not limited to, those which conform to the general formula (I):

$$(R_1)_a G_{3-a}-Si-(-OSiG_2)_n-(-OSiG_b(R_1)_{2-b})_m-O-SiG_{3-a}(R_1)_a$$

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; wherein when a is 0, b is not 2; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$A$^-$; —N($R_2$)$CH_2$—$CH_2$—N$R_2$$H_2$A$^-$; wherein $R_2$ is hydrogen, phenyl, benzyl, or a saturated hydrocarbon radical, preferably an alkyl radical from about $C_1$ to about $C_{20}$; A$^-$ is a halide ion.

A preferred amino silicone corresponding to formula (I) has m=0, a=1, q=3, G=methyl, n is preferably from about 1500 to about 1700, more preferably 1600; and L is —N(CH$_3$)$_2$. This is an example of a terminal aminosilicone, as there is a nitrogen group on one or both ends of the silicone chain.

A preferred aminosilicone corresponding to formula (I) is the polymer known as "trimethylsilylamodimethicone", which is shown below in formula (II):

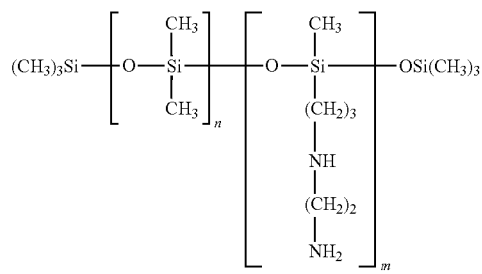

wherein n is a number from 1 to 1,999 and m is a number from 1 to 1,999.

Formula (II) is an example of a graft amino silicone, as there is a nitrogen group pendant to the silicone chain, but it is not on an end of the chain.

Other aminosilicone polymers which may be used in the compositions of the present invention are represented by the general formula (III):

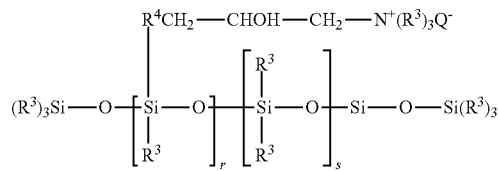

wherein $R^3$ is a monovalent hydrocarbon radical from $C_1$ to $C_{18}$, preferably an alkyl or alkenyl radical, such as methyl; $R^4$ is a hydrocarbon radical, preferably a $C_1$ to $C_{18}$ alkylene radical or a $C_{10}$ to $C_{18}$ alkyleneoxy radical, more preferably a $C_1$ to $C_8$ alkyleneoxy radical; Q$^-$ is a halide ion, preferably chloride; r is an average statistical value of from about 2 to about 20, preferably from about 2 to about 8; s is an average statistical value of from about 20 to about 200, preferably from about 20 to about 50, A preferred polymer of this class is known as UCARE SILICONE ALE 56™, available from Union Carbide.

B. Cationic Surfactant

The conditioning composition of the present invention comprises a cationic surfactant. The cationic surfactant is included in the composition at a level by weight of from about 0.1% to about 10%, preferably from about 1% to about 5%.

Cationic surfactants useful herein include, for example, those corresponding to the general formula (IV):

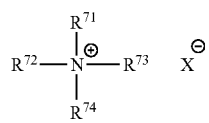

wherein at least one of $R^{71}$, $R^{72}$, $R^{73}$ and $R^{74}$ is selected from an aliphatic group of from about 8 to about 30 carbon atoms or an aromatic, alkoxy, polyoxyalkylene, alkylamido, hydroxyalkyl, aryl or alkylaryl group having up to about 22 carbon atoms, the remainder of $R^{71}$, $R^{72}$, $R^{73}$ and $R^{74}$ are independently selected from an aliphatic group of from about 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The aliphatic groups can contain, in addition to carbon and hydrogen atoms, ether, ester, or amido linkages and other groups such as amino groups. The longer chain aliphatic groups, (e.g., those of about 12 carbons, or higher), can be saturated, unsaturated, or branched. Preferred is when $R^{71}$, $R^{72}$, $R^{73}$ and $R^{74}$ are independently selected from $C_1$ to about $C_{22}$ alkyl. Nonlimiting examples of cationic surfactants useful in the present invention include the materials having the following CTFA designations: quaternium-8, quaternium-14, quaternium-18, quaternium-18 methosulfate, quaternium-24, and mixtures thereof.

Among the cationic surfactants of general formula (IV), preferred are those containing in the molecule at least one alkyl chain having at least 16 carbons. Nonlimiting examples of such preferred cationic surfactants include: behenyl trimethyl ammonium chloride available, for example, with tradename Genamine KDMP from Clariant, with tradename INCROQUAT TMC-80 from Croda, and with tradename ECONOL TM22 from Sanyo Kasei; cetyl trimethyl ammonium chloride available, for example, with tradename CTAC 30KC from KCI, and with tradename CA-2350 from Nikko Chemicals; stearyl trimethyl ammonium chloride available, for example, with tradename Genamine STACP from Clariant; olealkonium chloride available, for example, with tradename Incroquat O-50 from Croda; hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, distearyl dimethyl ammonium chloride, dicetyl dimethyl ammonium chloride, di(behenyl/arachidyl) dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methyl) pyridinium chloride.

Also preferred are hydrophilically substituted cationic surfactants in which at least one of the substituents contains one or more aromatic, ether, ester, amido, or amino moieties present as substituents or as linkages in the radical chain, wherein at least one of the $R^{71}$-$R^{74}$ radicals contain one or more hydrophilic moieties selected from alkoxy (preferably $C_1$-$C_3$ alkoxy), polyoxyalkylene (preferably $C_1$-$C_3$ polyoxyalkylene), alkylamido, hydroxyalkyl, alkylester, and combinations thereof. Preferably, the hydrophilically substituted cationic conditioning surfactant contains from about 2 to about 10 nonionic hydrophile moieties located within the above stated ranges. Highly preferred hydrophilically substituted cationic surfactants include dialkylamido ethyl hydroxyethylmonium salt, dialkylamidoethyl dimonium salt, dialkyloyl ethyl hydroxyethylmonium salt, dialkyloyl ethyldimonium salt, and mixtures thereof; for example, commercially available under the following tradenames; VARISOFT 110, VARISOFT 222, VARIQUAT K1215 and VARIQUAT 638 from Witco Chemical; MACKPRO KLP, MACKPRO WLW, MACKPRO MLP, MACKPRO NSP, MACKPRO NLW, MACKPRO WWP, MACKPRO NLP, MACKPRO SLP from McIntyre; ETHOQUAD 18/25, ETHOQUAD O/12PG, ETHOQUAD C/25, ETHOQUAD S/25, and ETHODUOQUAD from Akzo; DEHYQUAT SP from Henkel; and ATLAS G265 from ICI Americas. Babassuamidopropalkonium Chloride available from Croda under the tradename Incroquat BA-85 is also preferably used in the composition.

Amines are suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachnidamidopropyldimethylamine, arachidamidopropyldiethylamine, arachidamidoethyldiethylamine, arachidamidoethyldimethylamine, diethylaminoethylstearamide. Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidylbehenylamine. Useful amines in the present invention are disclosed in U.S. Pat. No. 4,275,055.

C. High Melting Point Fatty Compound

The hair conditioning composition of the present invention comprises a high melting point fatty compound. The high melting point fatty compound is a compound having the general formula R—X, wherein R is an aliphatic (e.g. fatty chain) and X is a functional group (e.g. alcohol, acid, or derivative). The high melting point fatty compound, together with the above cationic surfactant and an aqueous carrier, provides a gel matrix which is suitable for providing various conditioning attributes such as slippery and slick feel on wet hair, and softness, moisturized feel, fly-away control on dry hair, dry hair smoothness, hair strand alignment (e.g., minimize frizziness), and ease of combing.

Suitable high melting point fatty compounds useful herein have a melting point of 25° C. or higher, and are selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, (e.g. some fatty alcohol derivatives can also be classified as fatty acid derivatives). However, a given classification is not intended to be a limitation on that particular compound, but is done so for convenience of classification and nomenclature. Further, it is understood by the artisan that, depending on the number and position of double bonds and length and position of the branches, certain compounds having certain required carbon atoms may have a melting point of less than 25° C. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

The high melting point fatty compound can be included in the composition at a level of from about 0.1% to about 20%, preferably from about 1% to about 10%, still more preferably from about 2% to about 9%, by weight of the composition. It is preferred that the high melting point fatty compound is included at a level so that the mole ratio of the cationic surfactant to the high melting fatty compound is from about 1:2 to about 1:8.

The fatty alcohols useful herein are those having from about 14 to about 30 carbon atoms, preferably from about 16 to about 22 carbon atoms. These fatty alcohols are saturated and can be straight or branched chain alcohols. Nonlimiting examples of fatty alcohols include cetyl alcohol, stearyl alcohol, behenyl alcohol, and mixtures thereof.

The fatty acids useful herein are those having from about 10 to about 30 carbon atoms, preferably from about 12 to about 25 carbon atoms, and more preferably from about 16 to about 22 carbon atoms. These fatty acids are saturated and can be straight or branched chain acids. Also included are diacids, triacids, and other multiple acids which meet the requirements herein. Also included herein are salts of these fatty acids. Nonlimiting examples of fatty acids include lauric acid, palmitic acid, stearic acid, behenic acid, sebacic acid, and mixtures thereof.

The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, (e.g. a mixture of fatty alcohols containing predominantly cetyl and stearyl alcohol, wherein the numeric designation indicates the number of ethylene glycol moieties present); $C_1$-$C_{30}$ alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof.

High melting point fatty compounds of a single compound of high purity are preferred. Single compounds of pure fatty alcohols selected from the group consisting of pure cetyl alcohol, stearyl alcohol, and behenyl alcohol are highly preferred. By "pure" herein, what is meant is that the compound has a purity of at least about 90%, preferably at least about 95%. These single compounds of high purity provide good rinsability from the hair when the consumer rinses off the composition.

Commercially available high melting point fatty compounds useful herein include: cetyl alcohol, stearyl alcohol, and behenyl alcohol having tradenames KONOL series available from Shin Nihon Rika, and NAA series available from NOF; pure behenyl alcohol having tradename 1-DOCOSANOL available from WAKO, various fatty acids having tradenames NEO-FAT available from Akzo, HYSTRENE available from Witco Corp., and DERMA available from Vevy.

D. Aqueous Carrier

The conditioning composition of the present invention comprises an aqueous carrier. The level and species of the carrier are selected according to the compatibility with other components and other desired characteristics of the product.

The carrier useful in the present invention includes water and water solutions of lower alkyl alcohols and polyhydric alcohols. The lower alkyl alcohols useful herein are monohydric alcohols having 1 to 6 carbons, preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 95%, preferably from about 30% to about 92%, and more preferably from about 50% to about 90% of an aqueous carrier.

E. Optional Components

1. Low Viscosity Fluid

The compositions of the present invention may optionally comprise a low viscosity fluid to be mixed with the aminosilicone described above. The low viscosity fluid, when combined with the aminosilicone, serves to reduce the viscosity of the aminosilicone in order to facilitate the processing into the complete composition.

Concentrations of the low viscosity fluid in the conditioning compositions of the present invention will vary primarily with the type and amount of fluid and aminosilicone employed. Preferred concentrations of the low viscosity fluid are from about 0.1% to about 20%, preferably from about 0.1% to about 10% by weight of the composition.

Preferred low viscosity fluids are partially or completely miscible with the amino silicone and are effective at reducing the viscosity of the blend. The low viscosity fluid or combination of fluids should be used in the composition so that there is the least amount of low viscosity fluid as possible. When the two materials are blended, the preferred viscosity range will be from about 500 cs to about 100,000 cs, more preferably from about 1,000 cs to about 50,000 cs.

The low viscosity fluid for the aminosilicone is suitable for topical application to human hair and scalp. The low viscosity fluid is organic, silicone-containing or fluorine-containing, volatile or non-volatile, polar or non-polar, provided that the fluid is partially or completely miscible with the amino silicone and yields a mixture with the above stated viscosity.

The low viscosity fluid preferably includes volatile, non-polar oils; non-volatile, relatively polar oils; non-volatile, non-polar oils; and non-volatile paraffinic hydrocarbon oils. The term "non-volatile" as used herein refers to materials which exhibit a vapor pressure of no more than about 0.2 mm Hg at 25° C. at one atmosphere and/or to materials that have a boiling point at one atmosphere of at least about 300° C. The term "volatile" as used herein refers to all materials that are not "non-volatile" as previously defined herein. The phrase "relatively polar" as used herein means more polar than another material in terms of solubility parameter (e.g., the higher the solubility parameter the more polar the liquid). The term "non-polar" typically means that the material has a solubility parameter below about 6.5 $(cal/cm^3)^{0.5}$.

a. Non-polar, Volatile Oils

Non-polar, volatile oils particularly useful in the present invention are selected from the group consisting of silicone oils, hydrocarbons, and mixtures thereof. Such non-polar, volatile oils are disclosed, for example, in Cosmetics, Science, and Technology, Vol. 1, 27-104. The non-polar, volatile oils useful in the present invention may be either saturated or unsaturated, have an aliphatic character and be straight or branched chained or contain alicyclic or aromatic rings. Examples of preferred non-polar, volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals). Other isoparaffins include, for example, Isozol series available from Nippon Petrochemicals co., LTD, such as Isozol 200 (containing mainly C8 isoparaffin), Isozol 300 (containing mainly C12 isoparaffin), and Isozol 400 (containing mainly C14 isoparaffin). Non-polar, volatile hydrocarbons, especially non-polar, volatile isoparaffins are highly preferred among a variety of low viscosity fluids, in view of reducing the viscosity of the aminosilicones and providing improved hair conditioning benefits such as reduced friction on dry hair.

Non-polar, volatile liquid silicone oils are disclosed in U.S. Pat. No. 4,781,917. Additionally, a description of various volatile silicones materials is found in Todd et al., "Volatile Silicone Fluids for Cosmetics", Cosmetics and Toiletries, 91:27-32 (1976). Particularly preferred volatile silicone oils are selected from the group consisting of cyclic volatile silicones corresponding to the formula (V):

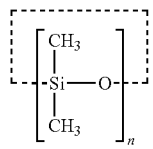

wherein n is from about 3 to about 7; and linear volatile silicones corresponding to the formula (VI):

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

b. Relatively Polar, Non-volatile Oils

The non-volatile oil is "relatively polar" as compared to the non-polar, volatile oil discussed above. Therefore, the non-volatile co-solvent is more polar (e.g., has a higher solubility parameter) than at least one of the non-polar, volatile oils. Relatively polar, non-volatile oils potentially useful in the present invention are disclosed, for example, in Cosmetics, Science, and Technology, Vol. 1, 27-104 edited by Balsam and Sagarin, 1972; U.S. Pat. Nos. 4,202,879 and 4,816,261. Relatively polar, non-volatile oils useful in the present invention are preferably selected from the group consisting of silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-solvents useful in the present invention may be either saturated or unsaturated, have an aliphatic character and be straight or branched chained or contain alicyclic or aromatic rings. More preferably, the relatively polar, non-volatile liquid co-solvents are selected from the group consisting of fatty alcohols having from about 12-26 carbon atoms; fatty acids having from about 12-26 carbon atoms; esters of monobasic carboxylic acids and alcohols having from about 14-30 carbon atoms; esters of dibasic carboxylic acids and alcohols having from about 10-30 carbon atoms; esters of polyhydric alcohols and carboxylic acids having from about 5-26 carbon atoms; ethoxylated, propoxylated, and mixtures of ethoxylated and propoxylated ethers of fatty alcohols with from about 12-26 carbon atoms and a degree of ethoxylation and propoxylation of below about 50; and mixtures thereof. More preferred are propoxylated ethers of C14-C18 fatty alcohols having a degree of propoxylation below about 50, esters of C2-C8 alcohols and C12-C26 carboxylic acids (e.g. ethyl myristate, isopropyl palmitate), esters of C12-C26 alcohols and benzoic acid (e.g. Finsolv TN supplied by Finetex), diesters of C2-C8 alcohols and adipic, sebacic, and phthalic acids (e.g., diisopropyl sebacate, diisopropyl adipate, di-n-butyl phthalate), polyhydric alcohol esters of C6-C26 carboxylic acids (e.g., propylene glycol dicaprate/dicaprylate, propylene glycol isostearate); and mixtures thereof. Even more preferred are branched-chain aliphatic fatty alcohols having from about 12-26 carbon atoms. Even more preferred are isocetyl alcohol, octyldecanol, octyldodecanol and undecylpentadecanol; and even more preferred is octyldodecanol.

c. Non-polar, Non-volatile Oils

In addition to the liquids discussed above, the low viscosity fluid may optionally include non-volatile, non-polar oils. Typical non-volatile, non-polar oils are disclosed, for example, in Cosmetics, Science, and Technology, Vol. 1, 27-104 edited by Balsam and Sagarin, 1972; U.S. Pat. Nos. 4,202,879 and 4,816,261. The non-volatile oils useful in the present invention are essentially non-volatile polysiloxanes, paraffinic hydrocarbon oils, and mixtures thereof. The polysiloxanes useful in the present invention selected from the group consisting of polyalkylsiloxanes, polyarylsiloxanes, polyalkylarylsiloxanes, poly-ethersiloxane copolymers, and mixtures thereof. Examples of these include polydimethyl siloxanes having viscosities of from about 1 to about 100,000 centistokes at 25° C. Among the preferred non-volatile silicone emollients useful in the present compositions are the polydimethyl siloxanes having viscosities of from about 2 to about 400 centistokes at 25° C. Such polyalkylsiloxanes include the Viscasil series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful polyethersiloxane copolymers include, for example, a polyoxyalkylene ether copolymer having a viscosity of from about 1200 to about 1500 centistokes at 25° C. Such a fluid is available as SF1066 organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375. Preferred mineral oils have the following properties:

(1) viscosity of from about 5 centistokes to about 70 centistokes at 40° C.;

(2) density of from about 0.82 to about 0.89 g/cm$^3$ at 25° C.;

(3) flash point of from about 138° C. to about 216° C.; and (4) carbon chain length of from about 14 to about 40 carbon atoms.

Preferred branched chain hydrocarbon oils have the following properties:

(1) density of from about 0.79 to about 0.89 g/cm3 at 20° C.;

(2) boiling point greater than about 250° C.; and (3) flash point of from about 110° C. to about 200° C.

Particularly preferred branched-chain hydrocarbons include Permethyl 103 A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp.

Additional solvents useful herein are described in U.S. Pat. No. 5,750,096.

2. Acid

The hair conditioning composition of the present invention may further comprise an acid selected from the group consisting of L-glutamic acid, lactic acid, hydrochloric acid, malic acid, succinic acid, acetic acid, fumaric acid, L-glutamic acid hydrochloride, tartaric acid, citric acid, and mixtures thereof; preferably L-glutamic acid, lactic acid, citric acid, and mixtures thereof. The amines herein are preferably partially neutralized with any of the acids at a molar ratio of the amine to the acid of from about 1:0.3 to about 1:2, more preferably from about 1:0.4 to about 1:1.3.

3. Polysorbate

The hair conditioning composition of the present invention preferably contains a polysorbate, in order to adjust rheology. Preferred polysorbates useful herein include polysorbate-20, polysorbate-21, polysorbate-40, polysorbate-60, and mixtures thereof. Highly preferred is polysorbate-20. The polysorbate can be contained in the composition at a level by weight of from about 0.01% to about 5%, preferably from about 0.05% to about 2%.

4. Polypropylene Glycol

Polypropylene glycols useful herein are those having a weight average molecular weight of from about 200 g/mol to about 100,000 g/mol, preferably from about 1,000 g/mol to about 60,000 g/mol. Without intending to be limited by theory, it is believed that the polypropylene glycol herein deposits onto, or is absorbed into hair to act as a moisturizer buffer, and/or provides one or more other desirable hair conditioning benefits.

The polypropylene glycol useful herein may be either water-soluble, water-insoluble, or may have a limited solubility in water, depending upon the degree of polymerization and whether other moieties are attached thereto. The desired solubility of the polypropylene glycol in water will depend in large part upon the form (e.g., leave-on, or rinse-off form) of the hair care composition. For example, in a rinse-off hair care composition, it is preferred that the polypropylene glycol herein has a solubility in water at 25° C. of less than about 1 g/100 g water, more preferably a solubility in water of less than about 0.5 g/100 g water, and even more preferably a solubility in water of less than about 0.1 g/100 g water.

The polypropylene glycol can be included in the hair conditioning composition of the present invention at a level of from about 0.01% to about 10%, preferably from about 0.05% to about 6%, more preferably from about 0.1% to about 3% by weight of the composition.

5. Low Melting Point Oil

Low melting point oils useful herein are those having a melting point of less than 25° C. The low melting point oil useful herein is selected from the group consisting of: hydrocarbon having from about 10 to about 40 carbon atoms; unsaturated fatty alcohols having from about 10 to about 30 carbon atoms such as oleyl alcohol; unsaturated fatty acids having from about 10 to about 30 carbon atoms; fatty acid derivatives; fatty alcohol derivatives; ester oils such as pentaerythritol ester oils, trimethylol ester oils, citrate ester oils, and glyceryl ester oils; poly α-olefin oils; and mixtures thereof. Preferred low melting point oils herein are selected from the group consisting of: ester oils such as pentaerythritol ester oils, trimethylol ester oils, citrate ester oils, and glyceryl ester oils; poly α-olefin oils; and mixtures thereof, Particularly useful pentaerythritol ester oils and trimethylol ester oils herein include pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO.

Particularly useful citrate ester oils herein include triisocetyl citrate with tradename CITMOL 316 available from Bernel, triisostearyl citrate with tradename PELEMOL TISC available from Phoenix, and trioctyldodecyl citrate with tradename CITMOL 320 available from Bernel.

Particularly useful glyceryl ester oils herein include triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

Particularly useful poly α-olefin oils herein include polydecenes with tradenames PURESYN 6 having a number average molecular weight of about 500 and PURESYN 100 having a number average molecular weight of about 3000 and PURESYN 300 having a number average molecular weight of about 6000 available from Exxon Mobil Co.

The low melting point oil can be included in the hair conditioning composition of the present invention at a level of from about 0.001% to about 10%, preferably up to about 5% by weight of the composition.

6. Cationic Polymer

Cationic polymers useful herein are those having an average molecular weight of at least about 5,000, typically from about 10,000 to about 10 million, preferably from about 100,000 to about 2 million.

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. Other suitable spacer monomers include vinyl esters, vinyl alcohol (made by hydrolysis of polyvinyl acetate), maleic anhydride, propylene glycol, and ethylene glycol. Other suitable cationic polymers useful herein include, for example, cationic celluloses, cationic starches, and cationic guar gums.

The cationic polymer can be included in the hair conditioning composition of the present invention at a level of from about 0.001% to about 10%, preferably up to about 5% by weight of the composition.

7. Polyethylene Glycol

Polyethylene glycol can also be used as an additional component. The polyethylene glycols useful herein correspond to the formula H(O—CH$_2$—CH$_2$)$_n$OH, wherein n is the number of ethoxy units. Polyethylene glycols useful herein include PEG-2M wherein n has an average value of about 2,000 (PEG-2M is also known as Polyox WSR® N-10 from Union Carbide and as PEG-2,000); PEG-5M wherein n has an average value of about 5,000 (PEG-5M is also known as Polyox WSR® N-35 and as Polyox WSR® N-80, both from Union Carbide and as PEG-5,000 and Polyethylene Glycol 300,000); PEG-7M wherein n has an average value of about 7,000 (PEG-7M is also known as Polyox WSR® N-750 from Union Carbide); PEG-9M wherein n has an average value of about 9,000 (PEG-9M is also known as Polyox WSR® N-3333 from Union Carbide); and PEG-14M wherein n has an average value of about 14,000 (PEG-14M is also known as Polyox WSR® N-3000 from Union Carbide).

The polyethylene glycol can be included in the hair conditioning composition of the present invention at a level of from about 0.001% to about 10%, preferably up to about 5% by weight of the composition.

8. Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel; vitamin E with tradename Emix-d available from Eisai; panthenol available from Roche; panthenyl ethyl ether available from Roche; hydrolysed keratin, proteins, plant extracts, and nutrients; emollients such as PPG-3 myristyl ether with tradename Varonic APM available from Goldschmidt; Trimethyl pentanol hydroxyethyl ether; PPG-11 stearyl ether with tradename Varonic APS available from Goldschmidt; Stearyl heptanoate with tradename Tegosoft SH available from Goldschmidt; Lactil (mixture of Sodium lactate, Sodium PCA, Glycine, Fructose, Urea, Niacinamide, Inositol, Sodium Benzoate, and Lactic acid) available from Goldschmidt; Ethyl hexyl palmitate with tradename Saracos available from Nishin Seiyu and with tradename Tegosoft OP available from Goldschmidt; hair-fixative polymers such as amphoteric fixative polymers, cationic fixative polymers, anionic fixative polymers, nonionic fixative polymers, and silicone grafted copolymers; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; salts, in general, such as potassium acetate and sodium chloride; coloring agents, such as any of the FD&C or D&C dyes; hair oxidizing (bleaching) agents, such as hydrogen peroxide, perborate and persulfate salts; hair reducing agents such as the thioglycolates; perfumes; sequestering agents, such as disodium ethylenediamine tetra-acetate; ultraviolet and infrared screening and absorbing agents such as octyl salicylate; and antidandruff agents such as zinc pyrithione and salicylic acid.

Method of Preparation

The hair conditioning compositions of the following examples can be prepared by any conventional method well known in the art. They are suitably made as follows:

Deionized water is heated to 85° C. and cationic surfactants and high melting point fatty compounds are mixed in. The water is maintained at a temperature of about 85° C. until the components are homogenized, and no solids are observed. The mixture is then cooled to about 55° C. and maintained at this temperature, to form a gel matrix. Aminosilicones, or a blend of aminosilicones and a low viscosity fluid, or an aqueous dispersion of an aminosilicione are added to the gel matrix. When included, poly α-olefin oils, polypropylene glycols, and/or polysorbates are also added to the gel matrix. The gel matrix is maintained at about 50° C. during this time with constant stirring to assure homogenization. After it is homogenized, it is cooled to room temperature. When included, other additional components such as perfumes and preservatives are added with agitation. A triblender and/or mill can be used in each step, if necessary to disperse the materials.

Method of Use

The conditioning compositions of the present invention are used in conventional ways to provide conditioning and other benefits. Such method of use depends upon the type of composition employed but generally involves application of an effective amount of the product to the hair or scalp, which may then be rinsed from the hair or scalp (as in the case of hair rinses) or allowed to remain on the hair or scalp (as in the case of gels, lotions, creams, and sprays). "Effective amount" means an amount sufficient enough to provide a dry conditioning benefit. In general, from about 1 g to about 50 g is applied to the hair or scalp.

Preferably, the composition is applied to wet or damp hair prior to drying of the hair. Typically, the composition is used after shampooing the hair. The composition is distributed throughout the hair or scalp, typically by rubbing or massaging the hair or scalp. After such compositions are applied to the hair, the hair is dried and styled in accordance with the preference of the user. In the alternative, the composition is applied to dry hair, and the hair is then combed or styled in accordance with the preference of the user.

NON-LIMITING EXAMPLES

The compositions illustrated in the following Examples exemplify specific embodiments of the compositions of the present invention, but are not intended to be limiting thereof. Other modifications can be undertaken by the skilled artisan without departing from the spirit and scope of this invention.

The compositions illustrated in the following Examples are prepared by conventional formulation and mixing methods. All exemplified amounts are listed as weight percents and exclude minor materials such as diluents, preservatives, color solutions, imagery ingredients, botanicals, and so forth, unless otherwise specified.

Example I

Example I demonstrates the surprising discovery that aminosilicones below a certain percent nitrogen range will provide a superior level of reduced friction on treated hair.

Table 1 shows the relationship between friction and percent nitrogen for amino functionalized silicone. Herein, "AP" is aminopropyl; herein, "AEAP" is aminoethylaminopropyl.

| Position | Amine Type | VISC | % N | Coef. of Friction |
|---|---|---|---|---|
| None | — | 350,000 | 0 | 0.390 |
| Term | AP | 412,000 | 0.022 | 0.298 |

Table 1 shows the relationship between friction and percent nitrogen for amino functionalized silicone. Herein, "AP" is aminopropyl; herein, "AEAP" is aminoethylaminopropyl.

| Position | Amine Type | VISC | % N | Coef. of Friction |
|---|---|---|---|---|
| Term | AP | 312,000 | 0.026 | 0.290 |
| Term | AP | 111,875 | 0.032 | 0.282 |
| Term | AP | 87,000 | 0.035 | 0.300 |
| Term | AP | 55,950 | 0.038 | 0.277 |
| Term | AP | 31,000 | 0.051 | 0.282 |
| Term | AP | 10,450 | 0.053 | 0.311 |
| Term | AP | 22,980 | 0.060 | 0.294 |

For this study, the silicone is dissolved in a volatile solvent, hexamethyl disiloxane (MM), and applied to hair (20 gram flat switch) or 2 gram paper strip (3 inches by 9 inches (7.62 cm×22.86 cm)) at a level of 1,000 ppm of silicone to hair/paper weight. The solvent is allowed to evaporate and the hair/paper is allowed to equilibrate in a 50% relative humidity overnight. The friction of the coated hair/paper is then measured using an Instron model 5542 (Instron, Inc.) to measure the force to drag a weighted sled (100 gms of weight) along the hair/paper in the with-cuticle direction.

Examples II-VI

| Ingredient | II | III | IV | V | VI |
|---|---|---|---|---|---|
| Glutamic Acid (1) | 0.640 | 0.640 | 0.640 | 0.640 | 0.640 |
| Stearamidopropyl Dimethylamine (2) | 2.000 | 2.000 | 2.000 | 2.000 | — |
| Behenamidopropyl Dimethylamine (3) | — | — | — | — | 2.300 |
| Cetyl Alcohol (4) | 2.500 | 2.500 | 2.500 | 2.500 | 2.500 |
| Stearyl Alochol (5) | 4.500 | 4.500 | 4.500 | 4.500 | 4.500 |
| Dimethicone (6) | 3.000 | 6.000 | — | — | 3.000 |
| Amodimethicone (7) | 2.000 | 4.000 | 2.000 | 2.000 | 2.000 |
| Dimethicone (8) | — | — | 3.000 | — | — |
| EDTA (9) | 0.100 | 0.100 | 0.100 | 0.100 | 0.100 |
| Benzyl Alcohol (10) | 0.400 | 0.400 | 0.400 | 0.400 | 0.400 |
| Methylchloroisothiazolinone, Methylisothiazolinone (11) | 0.0005 | 0.0005 | 0.0005 | 0.0005 | 0.0005 |
| Panthenyl Etheyl Ether (12) | 0.050 | 0.050 | 0.050 | 0.050 | 0.050 |
| Panthenol (13) | 0.050 | 0.050 | 0.050 | 0.050 | 0.050 |
| Perfume | 0.300 | 0.300 | 0.300 | 0.300 | 0.300 |
| Water | q.s. | q.s. | q.s. | q.s. | q.s. |

(1) L-Glutamic Acid, available from Orsan/Amylum
(2) Stearamidopropyldimethylamine (SAPDMA), available from Saci
(3) BAPDMA (IncromineBB), available from Croda
(4) Available from P&G Brooksland
(5) Available from P&G Brooksland
(6) TSF-451-20A (20 cs straight oil), available from GE
(7) Terminal aminosilicone, AP type, available from GE; viscosity range from 220,000-245,000
(8) Dow Corning 200 Fluid, 10 cs
(9) Ethylene Diamine Tetraacetic Acid (EDTA), available from BASF
(10) Available from Tessenderlo
(11) Kathon CG, available from Rohm & Haas
(12) dl-Pantyl, available from Dow Benelux
(13) Liquid dl-Panthenol (56% active), available from Dow Benelux -continued Table 1 shows the relationship between friction and percent nitrogen for amino functionalized silicone. Herein, "AP" is aminopropyl; herein, "AEAP" is aminoethylaminopropyl.

| Position | Amine Type | VISC | % N | Coef. of Friction |
|---|---|---|---|---|
| Term | AP | 12,338 | 0.070 | 0.298 |
| Graft | AEAP | 46,200 | 0.074 | 0.322 |
| Term | AP | 8,391 | 0.076 | 0.292 |
| Term | AP | 7,029 | 0.077 | 0.304 |
| Term | AP | 5,113 | 0.087 | 0.282 |
| Term | AEAP | 24,160 | 0.113 | 0.341 |
| Term | AP | 2,038 | 0.126 | 0.307 |
| Graft | AP | 191,800 | 0.164 | 0.426 |
| Graft | AEAP | 1,000,000+ | 0.176 | 0.401 |
| Graft | AEAP | 1,000,000+ | 0.182 | 0.386 |
| Graft | AP | 53,400 | 0.182 | 0.390 |
| Graft | AEAP | 78,400 | 0.196 | 0.338 |
| Graft | AEAP | 558,000 | 0.211 | 0.354 |
| Graft | AEAP | 1,000,000+ | 0.504 | 0.490 |
| Graft | AEAP | 98,500 | 0.616 | 0.472 |
| Graft | AP | 1,000,000+ | 0.616 | 0.520 |
| Graft | AP | 143,500 | 0.637 | 0.509 |

Examples VII-X

| Ingredient | VII | VIII | IX | X |
|---|---|---|---|---|
| Stearamidopropyl Dimethylamine (1) | — | — | — | 1.000 |
| Behentrimonium chloride/Isopropyl Alcohol (2) | 2.874 | 3.445 | 3.381 | — |
| Cetyl Alcohol (3) | 1.972 | 1.972 | 2.320 | 0.960 |
| Stearyl Alochol (4) | 3.553 | 3.553 | 4.180 | 0.640 |
| Dimethicone (5) | 3.000 | 3.000 | 3.000 | 3.000 |
| Amodimethicone (6) | 2.000 | 2.000 | 2.000 | 2.000 |
| EDTA (7) | — | — | — | 0.100 |
| Disodium EDTA (8) | 0.127 | 0.127 | 0.127 | — |
| Benzyl Alcohol (9) | 0.400 | 0.400 | 0.400 | 0.400 |
| Methylchloroisothiazolinone, Methylisothiazolinone (10) | 0.0005 | 0.0005 | 0.0005 | 0.0005 |
| Panthenyl Etheyl Ether (11) | 0.050 | 0.050 | 0.050 | 0.050 |
| Panthenol (12) | — | — | — | 0.050 |
| Panthenol (13) | 0.050 | 0.050 | 0.050 | — |
| Sodium Hydroxide (14) | 0.014 | 0.014 | 0.014 | — |
| Isopropyl Alcohol (15) | 0.764 | 0.916 | 0.899 | — |
| Citric Acid (16) | — | — | — | 0.130 |

| Ingredient | VII | VIII | IX | X |
|---|---|---|---|---|
| Quaternium-18 (17) | — | — | — | 0.750 |
| Hydroxyethylcellulose (18) | — | — | — | 0.250 |
| PEG-2M (19) | — | — | — | 0.500 |
| Polysorbate 60, Cetearyl Alcohol (20) | — | — | — | 0.500 |
| Glyceryl Stearate (21) | — | — | — | 0.250 |
| Oleyl Alcohol (22) | — | — | — | 0.250 |
| Perfume | 0.300 | 0.300 | 0.300 | 0.250 |
| Water | q.s. | q.s. | q.s. | q.s. |

(1) Stearamidopropyldimethylamine (SAPDMA), available from Saci
(2) BTMAC/IPA (Genamin KDMP), available from Clariant
(3) Available from P&G Brooksland
(4) Available from P&G Brooksland
(5) TSF-451-20A (20 cSt straight oil), available from GE
(6) Terminal aminosilicone, AP type, available from GE; viscosity range from 220,000-245,000
(7) Ethylene Diamine Tetraacetic Acid (EDTA), available from BASF
(8) Disodium EDTA, available from SCAL
(9) Available from Tessenderlo
(10) Kathon CG, available from Rohm & Haas
(11) dl-Pantyl, available from Dow Benelux
(12) dl-Panthenol (powder), available from Dow Benelux
(13) Liquid dl-Panthenol (56% active), available from Dow Benelux
(14) Sodium Hydroxide (NaOH), available from Kaneda
(15) IPA (as solvent for BTMAC)
(16) Available from Jungbunzlauer
(17) Distearyldimethylammonium Chloride (DSDMAC), available from Goldschmidt
(18) Available from Hercules/Aqualon
(19) PEG-2M (Polyox WARN-10), available from Amerchol
(20) Emulsifying Wax (Polawax NF), available from Croda
(21) Glyceryl Monostearate (GMS), available from Surfachem
(22) Available from NJC/Tomen

Examples XI-XV

| Ingredient | XI | XII | XIII | XIV | XV |
|---|---|---|---|---|---|
| Behentrimonium chloride (1) | 2.250 | 2.250 | 3.381 | 3.381 | — |
| Isopropyl Alcohol (1) | 0.598 | 0.598 | 0.899 | 0.899 | — |
| Stearamidopropyldimethylamine (2) | — | — | — | — | 2.000 |
| L-Glutamic acid (3) | — | — | — | — | 0.640 |
| Cetyl Alcohol (4) | 1.857 | 1.857 | 2.320 | 2.320 | 2.500 |
| Stearyl Alochol (5) | 4.642 | 4.642 | 4.180 | 4.180 | 4.200 |
| Amodimethicone (6) | 3.500 | 3.500 | 3.500 | 3.500 | 4.200 |
| Isoparaffin (7) | 1.500 | — | 1.500 | — | 6.300 |
| Disodium EDTA (8) | 0.127 | 0.127 | 0.127 | 0.127 | — |
| EDTA (9) | — | — | — | — | 0.1 |
| Benzyl Alcohol (10) | 0.400 | 0.400 | 0.400 | 0.400 | 0.400 |
| Methylchloroisothiazolinone, Methylisothiazolinone (11) | 0.0005 | 0.0005 | 0.0005 | 0.0005 | 0.0005 |
| Panthenyl Etheyl Ether (12) | 0.050 | — | — | 0.050 | 0.050 |
| Panthenol (13) | 0.050 | — | — | 0.050 | 0.050 |
| Sodium Hydroxide (14) | 0.014 | 0.014 | 0.014 | 0.014 | — |
| Perfume | 0.500 | 0.500 | 0.500 | 0.500 | 0.500 |
| Water | q.s. | q.s. | q.s. | q.s. | q.s. |

(1) BTMAC/IPA (Genamin KDMP), available from Clariant
(2) Stearamidopropyldimethylamine, available from Saci
(3) L-Glutamic acid, available from Orsan/Amylum
(4) Available from P&G Brooksland
(5) Available from P&G Brooksland
(6) Terminal aminosilicone, AP type, available from GE; viscosity range from 220,000-245,000
(7) Isozol 400 (a mixture of C11-C16 isoparaffins containing about 41% of C14 isoparaffin), available from Nippon Petrochemicals co., LTD.
(8) Available from SCAL
(9) Ethylene Diamine Tetraacetic Acid (EDTA), available from BASF
(10) Available from Tessenderlo
(11) Kathon CG, available from Rohm & Haas
(12) dl-Pantyl, available from Dow Benelux
(13) Liquid dl-Panthenol, available from Dow Benelux
(14) Sodium Hydroxide (NaOH), available from Kaneda While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

All documents cited in the Background, Summary of the Invention, and Detailed Description of the Invention are, in relevant part, incorporated herein by reference; the citation of any document is not to be construed as an admission that it is prior art with respect to the present invention.

What is claimed is:

1. A hair conditioning composition comprising:

(1) a terminal aminosilicone having chemical formula $(R_1)_a G_{3-a}—Si(OSiG_2)_n\ —(—OSiG_b(R_1)_{2-b})_m—O—SiG_{3-a}$ wherein G is methyl, monovalent radical conforming to the formula $C_q H_{2q} L$, a=1, b=2, n is from about 1500 to about 17000; m=0; q is 3; and L is $—N(CH_3)_2$ (2) from about 0.1% to about 10% of behenyl trimethyl ammonium chloride;

(3) a high melting point fatty compound wherein said high melting fatty compound is selected from the group consisting of cetyl alcohol, stearyl alcohol and behenyl alcohol wherein said high melting fatty compound is present at a level of from about 0.1% to about 20%;

(4) from about 0.1% to about 20% of low viscosity fluid, where in said low viscosity fluid comprises a non-polar, volatile hydrocarbon (5) an acid
(6) from about 0.01% to about 5% polysorbate
(7) from about 0.01% to about 10% polypropylene glycol and an aqueous carrier said terminal aminosilicone is present in the composition in an amount of from about 0.1% to about 20%.

2. The conditioning composition according to claim 1 wherein said aminosilicone is present in the composition in an amount of from about 0.5% to about 10%.

3. The conditioning composition according to claim 2 wherein said terminal aminosilicone is present in the composition in an amount of from about 1% to about 6%.

4. A method conditioning hair comprising the steps of applying said conditioning composition according to claim 1 to hair and rinsing.

* * * * *